US00PP20859P3

(12) United States Plant Patent
Catena

(10) Patent No.: US PP20,859 P3
(45) Date of Patent: Mar. 23, 2010

(54) GRAPEVINE NAMED 'CATENA MALBEC CLONE 13'

(50) Latin Name: *Vitis vinifera*
Varietal Denomination: Catena Malbec Clone 13

(75) Inventor: Nicolas Catena, Mendoza (AR)

(73) Assignee: Bodegas Y Vinedos Nicolas Catena SA, Mendoza (AR)

( * ) Notice: Subject to any disclaimer, the term of this patent is extended or adjusted under 35 U.S.C. 154(b) by 0 days.

(21) Appl. No.: 12/072,554

(22) Filed: Feb. 26, 2008

(65) Prior Publication Data

US 2009/0217433 P1 Aug. 27, 2009

(51) Int. Cl.
*A01H 5/00* (2006.01)

(52) U.S. Cl. ..... Plt./205

(58) Field of Classification Search ..... Plt./205
See application file for complete search history.

(56) References Cited

OTHER PUBLICATIONS

NY *Vitis vinifera* variety studies—details for Cold Hardiness of PN Clones [online], [retrieved on Feb. 17, 2009]. Retrieved from the Internet <http://www.nysaes.cornell.edu/hort/faculty/pool/pinot-noir-folder/pnresults1.html> 3 pages.*

Internet Archive Wayback Machine [online] [retrieved on Feb. 17, 2009]. Retrieved from the Internet <http://web.archive.org/web/> 1 page.*

Vail, M. E. et al. (Jan. 1998). "Effect of Cluster Tightness on Botrytis Bunch Rot in Six Chardonnay Clones," *Plant Disease* 82(1): 107-109.

U.S. Office Action mailed Feb. 13, 2009, for U.S Appl. No. 12/072,674 filed Feb. 26, 2008, 13 pages.

U.S. Office Action mailed Feb. 13, 2009, for U.S Appl. No. 12/072,553 filed Feb. 26, 2008, 13 pages.

U.S. Office Action mailed Feb. 25, 2009, for U.S Appl. No. 12/072,582 filed Feb. 26, 2008, 9 pages.

U.S. Appl. No. 12/072,553, filed Feb. 26, 2008 Catena.

U.S. Appl. No. 12/072,555, filed Feb. 26, 2008 Catena.

U.S. Appl. No. 12/072,582, filed Feb. 26, 2008 Catena.

U.S. Appl. No. 12/072,674, filed Feb. 26, 2008 Catena.

Vail, M. E. et al. (Jan. 1998). "Effect of Cluster Tightness on Botrytis Bunch Rot in Six Chardonnay Clones," *Plant Disease* 82(1):107-109.

* cited by examiner

*Primary Examiner*—June Hwu
(74) *Attorney, Agent, or Firm*—Morrison & Foerster LLP

(57) ABSTRACT

A distinct Malbec grape variety from Mendoza Argentina, herewith denominated 'Catena Malbec Clone 13' which shows a unique vineyard and winemaking profile from the rest of the Malbec grapevine population in Mendoza, Argentina. This Malbec grape variety is characterized by its medium cluster size and weight; compact cluster form; medium berry size and weight; medium vigor; low level of *millendrage* (shot berries); medium—high level of polyphenols and tannins; high aromatic intensity and excellent mid-palate flavor depth.

5 Drawing Sheets

Botanical/commercial classification: *Vitis vinifera* L. Variety Denomination: 'Catena Malbec Clone 13'.

BACKGROUND OF THE INVENTION

Once known as a variety of Bordeaux, the Malbec grape is now being cultivated in South America, including Argentina. Malbec grapes produce outstanding red wines with characteristics that generally fall somewhere between Cabernet Sauvignon and Merlot.

Historically, Argentine vintners did not engage in selecting grape varieties. A less than rigorous attention to grape variety selection meant that Malbec vineyards in Mendoza consisted of populations of a highly heterogeneous, haphazard mix of grape varieties throughout the vineyard. There is a need for distinct Malbec grape varieties with improved quality based characteristics such as low yield, plant balance, and fruit concentration.

In the following description, the color-coding is in accordance with the Horticultural Colour Chart of The Royal Horticultural Society, London, England (R.H.S. Colour Chart).

BRIEF SUMMARY OF THE INVENTION

The present invention relates to a newly selected and distinct Malbec grape variety of the Malbec grapevine, *Vitis vinifera* L., which will hereinafter be denominated as the 'Catena Malbec Clone 13'. The present plant, however, is different from the other Malbec varieties in at least, but not limited to, the attributes as specified in detail below. 'Catena Malbec Clone 13' has medium cluster size and weight; compact cluster form; medium berry size and weight; medium vigor; low level of *millendrage* (shot berries); medium to high level of polyphenols and tannins; high aromatic intensity and excellent mid-palate flavor depth.

DETAILED DESCRIPTION OF THE INVENTION

Figure 1:
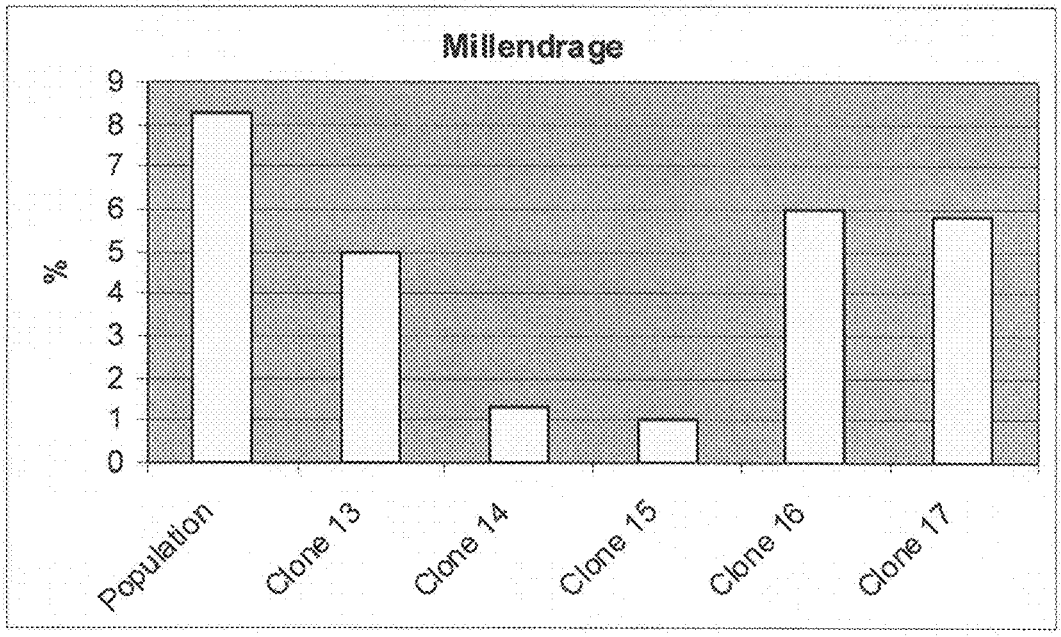
FIG. 1: Total millendrage of the diverse Malbec grapevine plant population and of selected varieties (Clones 13 to 17).

The Malbec grape variety 'Catena Malbec Clone 13' of the present invention originated from a very demanding selection process originating from the present grape variety that was selected in 1992 from a diverse Malbec grapevine population and which has been asexually reproduced by self rooted cuttings. That present grape variety was an unknown naturally occurring mutation of Malbec vines showing desirable characteristics as detailed below. The selection process began in 1992 and was carried out in Mendoza, Argentina.

The process began with a selection of genetically diverse parent plants of the Malbec grapevine plant population with unknown natural mutations. The selections were then asexually reproduced by self rooted cuttings. During three growing seasons, all selected plants were systematically observed in a vineyard in the Lunlunta district of the Maipu region of Mendoza, Argentina.

The goal was to identify a wide base of genetic profiles. The first criteria were to select those Malbec vines which showed overall good health and good fruit set. The next criterion was diversity, identifying those plants with varying levels of vigor; different dates of budbreak and harvest; and varying sizes of clusters and berries. Malbec grape varieties fitting these criteria were marked for further study.

This preliminary selection process resulted in the identification of 108 different Malbec grape varieties from the vineyard, located in the Lunlunta district of the Maipu region of Mendoza, Argentina.

All of the selected 108 varieties were then subjected to an ELISA test to detect for Arabis mosaic virus, Grapevine fleck virus, Grapevine fanleaf virus, Grapevine leafroll associated virus Types 1, 2, 3, and Tomato ringspot virus. Each grape variety was then multiplied from bi-nodal pruned budwood using micro-propagation techniques. This method ensured the overall good health of the multiplied plants.

A total of 51 to 55 micro-propagated plants from each grape variety successfully passed through the process of propagation and rustication, and having achieved the dimensions necessary to survive in the field, were planted in 1994 in a vineyard, located in the Agrelo district of the Lujan de Cuyo region of Mendoza, Argentina. The Malbec grape varieties were planted at a density of two meters between rows and 1.25 meters between plants and trained to a vertical shoot positioned trellis. All plants were pruned to a double Guyot system of loading canes with an average of 9 to 12 buds per cane.

The objective of the Malbec grapevine selection originating from a genetically diverse population with unknown naturally occurring mutations was to identify those grape varieties which possessed both vineyard performance and wine quality characteristics which were above the level achieved for the general population of Malbec grapevines.

The vineyard performance criteria included overall grapevine development, shoot growth rate, plantation failures, dates of budbreak, veraison and harvest, compactness, size, number of clusters, size, number, and millendrage level of berries, susceptibility to mildew, as well as brix, pH, acidity and anthocyanin levels. Given that the end goal of this selection process was to improve the overall quality of Malbec wine produced, certain elements of the above criteria were given more weight than others:

Color: Plants with overall high anthocyanin counts were given additional weight in the selection. Low anthocyanin count resulted in elimination from the selection.

Brix, acidity and pH Levels: Proper development of these elements throughout the growing season as well as balance at the moment of harvest were important criteria for selection.

Berry size: The selection process sought to identify Malbec grape varieties with a high ratio of skin to juice, generally seeking smaller berries.

Millendrage: Malbec grape varieties were chosen for low levels of millendrage and shot berries, seeking even fruit set.

In 1997 fifteen grape varieties were selected with optimal vineyard performance (low yields, small clusters, small berries, high polyphenols and low millendrage) and varying yet complimentary flavor profiles. These fifteen varieties were vinified separately and characteristics (aroma, concentration, natural acidity, ripening time, typicity, astringency, flavor sensation) were compared.

In 1998 the five best grape varieties were selected using the joint vineyard and wine criteria described above. These were also sent to the University of Adelaide for virus testing, which turned out negative for all tested samples.

In 1999 the original 108 selected different Malbec grape varieties, including the five best varieties from 1998, were planted at 5,000 feet above sea level in the Gualtallary district of the Tupungato region in Mendoza, Argentina.

In 2002 using the same selection process as originally implemented, grape varieties 'Catena Malbec Clone 13' and 'Catena Malbec Clone 17' U.S. Plant application Ser. No. 12/072,582 were selected as optimum for this vineyard site and planted in an experimental 3 hectare block.

In 2003 the five selected grape varieties were planted at 3,870 feet above sea level in the Altamira district of the San Carlos region in Mendoza.

In 2007 the selected five grape varieties, 'Catena Malbec Clone 13' to 'Catena Malbec Clone 17' passed a three year viral field study conducted by the Foundation Plant Services Department at the University of California Davis. They have recently been released from quarantine after having passed all pertinent viral tests and are currently being held at a vineyard in California.

DETAILED BOTANICAL DESCRIPTION

Below is a detailed botanical description of the distinct grape variety 'Catena Malbec Clone 13':

VINE Generally: Size.—medium grapevine size as determined on grapevines growing on a three wire vertical shoot positioned trellis with the first wire (fruit zone) set 80 cm (31.25 inches) above the ground; the second wire at 1.30 m (50.78 inches) above the ground; and the third wire at 1.8 m (70.31 inches) above the ground. The vine was trained to produce a grapevine height of 2.03 m (79.92 inches) and a grapevine spread of 37 cm (14.56 inches). Vigor.—medium vigor. Vigor as measured by weighing prunings at dormant pruning for cane pruned grapevines (with 14 canes and an average of 16 buds per cane) was 1.144 Kg. Productivity.—Productive. 1.8 Kg per grapevine as compared to the average population grapevine which produces 1.55 Kg per grapevine on grapevines spaced 4.1 ft. (125 cm) by 6.5. (200 cm). Regularity of bearing.—Regular. Annual pruning of canes is required for reliable production.

CANES Size: Diameter—mature canes.—Medium diameter. medium vigor. upright in growth habit. Mature canes: Diameter—internode base.—8.5 mm (0.332 inches). Diameter—internode midpoint.—8 mm (0.3125 inches). Diameter—internode tip.—4 mm (0.156 inches). Diameter—node base.—10.1 mm (0.429 inches). Diameter—node midpoint.—12 mm (0.468 inches). Diameter—node tip.—6.5 mm (0.254inches). Internode length: Base.—5.9 cm (2.3 inches). Midpoint.—7.85 cm (3.06 inches). Tip.—8.2 cm (3.2 inches). Average length of canes.—123 cm (48.42 inches). Surface texture.—Smooth. Color of mature cane.—Brown (Plate 11 H7). No anthocyanin observed on mature canes. Buds: Color.—Brown (Plate 13 H9). Texture.—Smooth. Dormant bud (compound bud or eye): Width.—At base of cane 4 mm (0.156 inches); at midpoint of cane 4.2 mm (0.164 inches) and at tip of cane 3.1 mm (0.121 inches). The average number of buds on a current. single-season growth cane is 16. Date of bud break.—October 7. midseason. Young shoots.—Surface texture.—smooth. Young shoots have cobwebby indument. Diameter of young shoots in spring (measured when shoots are 24 inches).—At base 6 mm (0.234 inches). at midpoint 0.46 mm (0.179 inches) and at tip 3.1 mm ( 0.121 inches). Internode length.—3.9 cm (1.523 inches) at 4 cm (1.575 inches) internode from base. Young shoots: Color.—Pale green (Plate 18 L7). Stem of shoot tip: Color.—Green (Plate 20 L6) and ocassional red (plate 6 I4). Shoot: Shape.—Straight to slightly curved. Shoot tip: Form.—Open. Tendrils: Size.—Length—17.5 cm (6.83 inches). Size.—Diameter—1.75 mm (0.683 inches). Shape.—Usually biforcated and curled on distal end. Surface texture.—smooth. Pattern.—Found beginning opposite node 6 and 7 then again at nodes 9, 10, 12, 13, 15, 16 with this repeating intermittent pattern to the distal end of the cane. Tendril: Color immature growth.—Yellow green (Plate 21 L6). Disease resistance: Susceptible to Odium and Downey & Powdery Mildew. and fungicides were applied to the grapevines under evaluation to control them. Insect resistance: There has been no insect resistance detected given that insects are very rare in Mendoza.

LEAVES Size: Generally.—Leaves simple and alternate. The mid vein (L1) is 11.4 cm (4.45 inches) long. vein L2 is 9.4 cm ( 3.68 inches) long and vein L3 is 6.6 cm ( 2.57 inches) long. The angle between the mid vein L1 and L3 is 65 degrees and between L1 and the 1st vein off L3 is 145 degrees. Average length.—15.6 cm (6.09 inches). Average width.—14.3 cm (5.59 inches). Shape.—Orbicular. Lobes: Number.—five (5). three (3) without lobes. Color: Upwardly disposed surface.—Dark green (Plate 23 H10).Upward surface is glabrous. flat and smooth to slightly bullate. Downwardly disposed surface.—Green (Plate 22 I6). Lower surface has short hairs. Leaf vein.—Light green (Plate 19 I6) with occasional red (Plate 6 I4) on main veins near center of leaf. Leaf vein—thickness.—Thickness of mid vein at center of leaf is 1.5 mm (0.058 inches). Leaf margin.—Serrated with shape of teeth pointed and medium in size (convex teeth). Petiole sinus.—Half open and "V" shape. On mature leaf is 3.4 cm (1.33 inches) deep and 1 cm (0.39 inches) wide at widest point. Anthocyanin: Main veins—location.—With occasional red on main veins near center of leaf. Petiole: Size.—Medium. Length.—7.5 cm (2.92 inches). Diameter.—2.4 mm (0.128 inches). Surface texture.—smooth. Color.—Green (Plate 20 L4) with occasional red (Plate 6 I4) covering. Color: Young leaf—upper surface.—Pale green (Plate 21 L8) with light copper (Plate 19 I6) and cobwebby indument on upper surface. Young leaf—lower surface.—Pale green (Plate 22 K7). Shape unfolded—young leaf.—Concave to flat. Petiole of young leaf—color.—Medium green (Plate 21 L8). Stipules.—Green (Plate 21 L7).

TRUNK Size: Large. Height.—Approximately 75 cm (29.3 inches) above the vineyard floor. Diameter.—13.5 cm (5.66 inches) as measured just below the cordon or head point at 40 cm (15.6 inches) above vineyard floor.

FLOWERS Flower: Size—generally.—Medium. Unopened—diameter.—1.7 mm (0.066inches). Unopened—length.—1.6 mm (0.062 inches). Unopened—surface texture.—Smooth. Date of bloom.—First bloom November 10. Date of full bloom.—November 17 at 90%. Inflorescence.—Panicle. Fragrance: no fragrance.—Cluster size: At bloom.—Generally. medium. Cluster—length.—13.8 cm (5.39 inches). Width.—12.5 cm (4.88 inches). Peduncle: Length.—2.8 cm (1.09 inches). Color.—Green (Plate 20 L8). Shape of cluster.—Conical. Flower (calyptra): Color.—Green (Plate 20 L6). Stamens.—Five (5) Pistil.—Well developed. Ovary: Color.—Green (Plate 20 L8). Pollen.—Normal. fertile. abundant. Anthers: Color.—Straw (Plate 10 G2).

FRUIT: Maturity when described: Ripe for commercial harvesting and shipment approximately March 10 in Mendoza. Argentina. Cluster (Bunch): Size—cane pruned vines.—113.5 grams (3.98 oz). Length.—15.29 cm (6.01 inches). Width.—14.4 cm (5.62 inches). Shape.—Conical. Density.—Tight. on average has 101 berries per cluster. Clusters per vine.—15. Clusters per shoot.—1.04 clusters per shoot. Peduncle: Size: Length.—Medium. 4 cm (1.56 inches). Diameter.—Medium. 4.65 mm (0.181 inches). Color.—Green (plate 20 K6). Texture.—Smooth. glabrous. Pedicel: Generally.—There is a medium to good attachment between the berry and the pedicel. Size—length.—5.4 mm (0.21 inches). Size—diameter.—0.7 mm (0.027 inches). Color.—Green (Plate 20 H7).Texture.—Glabrous. Brush: Length.—1.9 mm (0.074 inches). Brush color.—Green (Plate 20 D2). Berry: Size.—Medium. avg. 1.09 grams (0.038 oz). Shape.—spherical 1.3 cm (0.507 inches) long and 1.2 cm (0.468 inches) wide. Number of seeds per berry.—4 seeds. Color.—Raspberry red (Plate 6 I15). Bloom.—Light. Skin: color.—Deep purple (Plate 6 C6). Thickness.—Medium in thickness. Texture.—Smooth. Tendency to crack.—None. Flesh: Flesh color.—Translucent and very pale green (Plate 18 B1). Texture.—Firm. meaty. Juice production.—High Color of juice.—Clear (Plate 19 B1). Flavor.—Sweet and sub acid flavor. Soluble solids.—24.4%. Titratable acid.—3.58g/L ml juice. Aroma.—None. Ripening.—Uniform. Character of seeds: Complete seeds. Seed color is auburn (Plate 7 C11). Use: wine. Resistance to disease: No resistance to Downey & Powdery Mildew or Odium.

Below are comparative tables (Table 1 and 2) and figures (FIGS. 1 to 4) to demonstrate the differences found in the selected Malbec grape varieties.

Table 1 reveals different physiological characteristics between 'Catena Malbec Clone 13' and the other 4 selected Malbec grape varieties (Clones 14 to 17) as well as the overall population.

TABLE 1

| | Clone 13 | Clone 14 | Clone 15 | Clone 16 | Clone 17 | Population |
|---|---|---|---|---|---|---|
| Potential Foliage Surface Area m2 | 4.2 | 6.2 | 3.6 | 4.1 | 5.3 | 3.62 |
| No. Shoots | 14.3 | 12.6 | 12.8 | 12.8 | 14.2 | 12.6 |

TABLE 1-continued

| | Clone 13 | Clone 14 | Clone 15 | Clone 16 | Clone 17 | Population |
|---|---|---|---|---|---|---|
| Avg. Shoot Length (cm) | 123.0 | 152.1 | 76.0 | 138.4 | 141.4 | 94.3 |
| Pruned Material Weight m/g | 1144.0 | 919.8 | 870.4 | 978.1 | 1202.3 | 917.4 |
| Exposed Surface Area/ Production | 1.64 | 1.74 | 1.42 | 1.53 | 1.72 | 0.98 |
| No. of Leaf Layers | 3.6 | 2.5 | 2.6 | 2.9 | 3.3 | 2.7 |

The Malbec grapevine plant has a tendency for shot berries causing problems with homogeneity and cluster ripening. Homogeneity is a key factor for quality. FIG. 1 depicts differences in millendrage between 'Catena Malbec Clone 13' and the other 4 selected Malbec grape varieties (Clones 14 to 17) as well as the overall population.

In addition, Table 2 shows some of the physiological characteristics and individuality of the 'Catena Malbec Clone 13' variety, when compared to the other selected Malbec grape varieties (Clones 14 to 17) and to the overall Malbec grapevine population.

TABLE 2

| Clone | Cluster Length | Cluster Weight | Total Berry Weight | No. of Berries | Berry Weight | Compact Index |
|---|---|---|---|---|---|---|
| 13 | 15.29 cm | 113.54 gr | 110.11 gr | 101.1 | 1.09 gr | 0.15 |
| 14 | 16.84 cm | 128.9 gr | 97.76 gr | 97 | 1.01 gr | 0.17 |
| 15 | 16.32 cm | 69.42 gr | 69.75 gr | 65.7 | 1.06 gr | 0.25 |
| 16 | 14.63 cm | 119 gr | 88 gr | 89 | 0.99 gr | 0.16 |
| 17 | 8.32 cm | 47.5 gr | 37.8 gr | 34.2 | 1.11 gr | 0.24 |
| Population | 18.23 cm | 91.68 gr | 85.06 | 83.11 | 1.02 | 0.22 |

Figure 2:
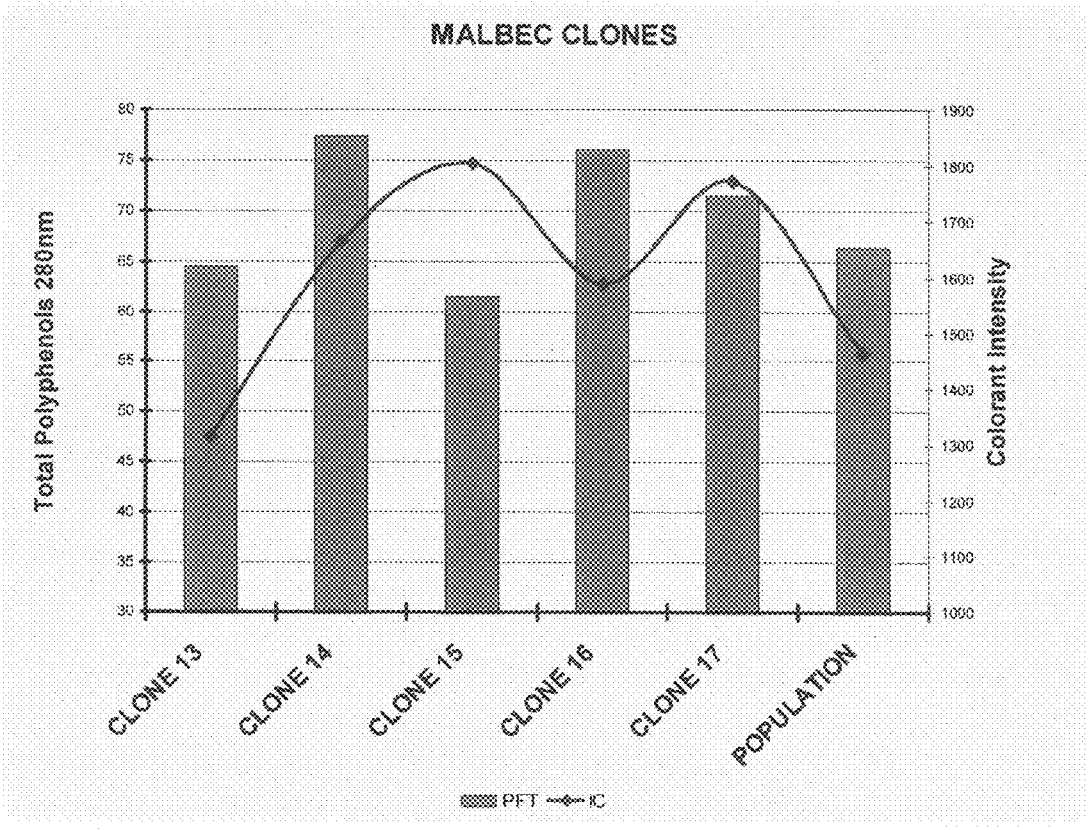
FIG. 2: Total polyphenols of the diverse Malbec grapevine plant population and of selected varieties (Clones 13 to 17).
Figure 3:
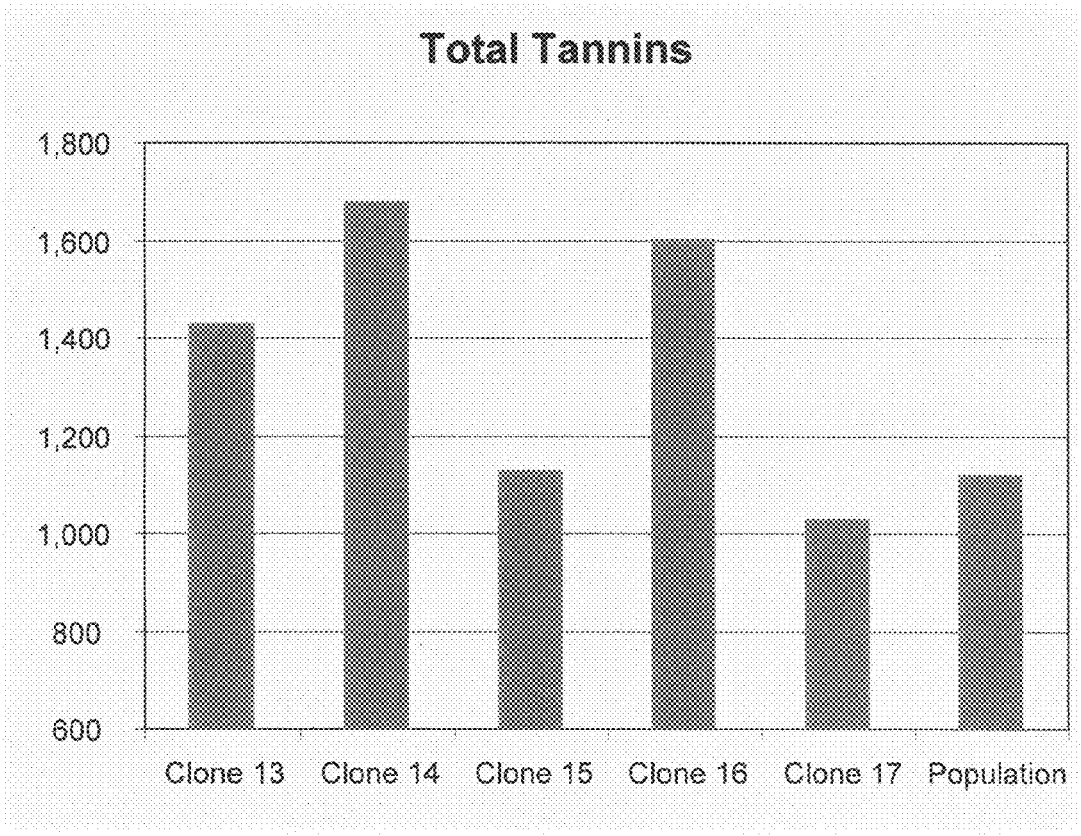
FIG. 3: Total tannins of the diverse Malbec grapevine plant population and of selected varieties (Clones 13 to 17).

The individuality of the Malbec grape variety 'Catena Malbec Clone 13' was also measured in terms of its chemical profile when compared to other selected Malbec grape varieties (Clones 14 to 17) and the overall Malbec grapevine population. Total polyphenols are shown in FIG. 2. Total tannins are graphed in FIG. 3.

Figure 4:
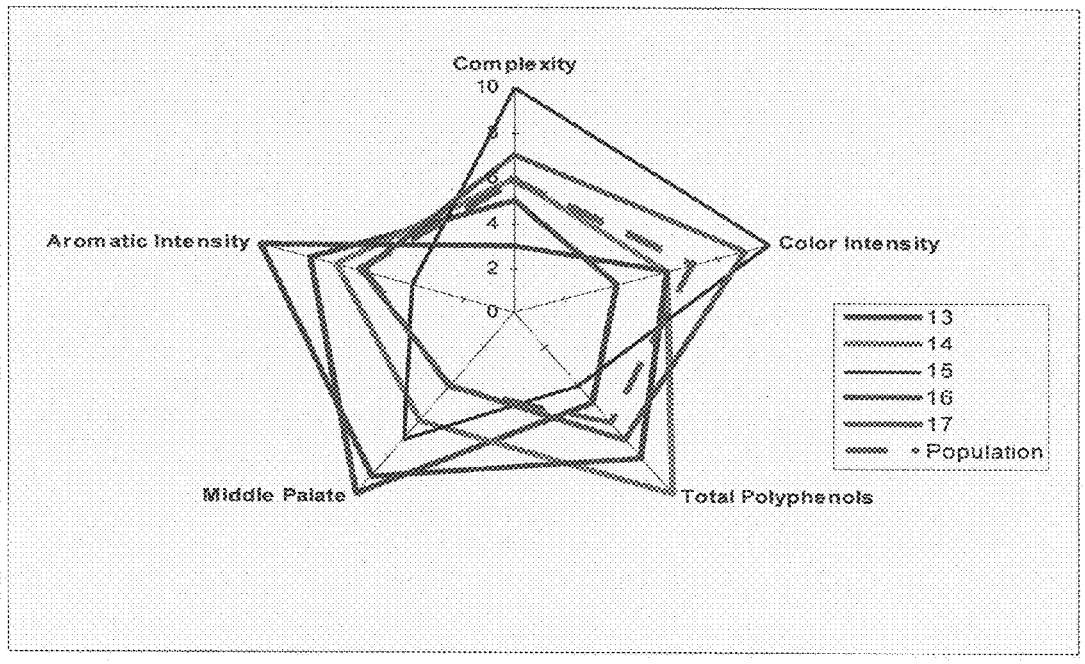
FIG. 4: Aroma and flavour profile of the diverse Malbec grapevine plant population and of selected varieties (Clones 13 to 17).

The 'Catena Malbec Clone 13' was also measured in terms of its aroma and flavor profile when compared to the other selected Malbec grape varieties (Clones 14 to 17) and the overall Malbec grapevine population. The results are shown in FIG. 4.

Figure 5:
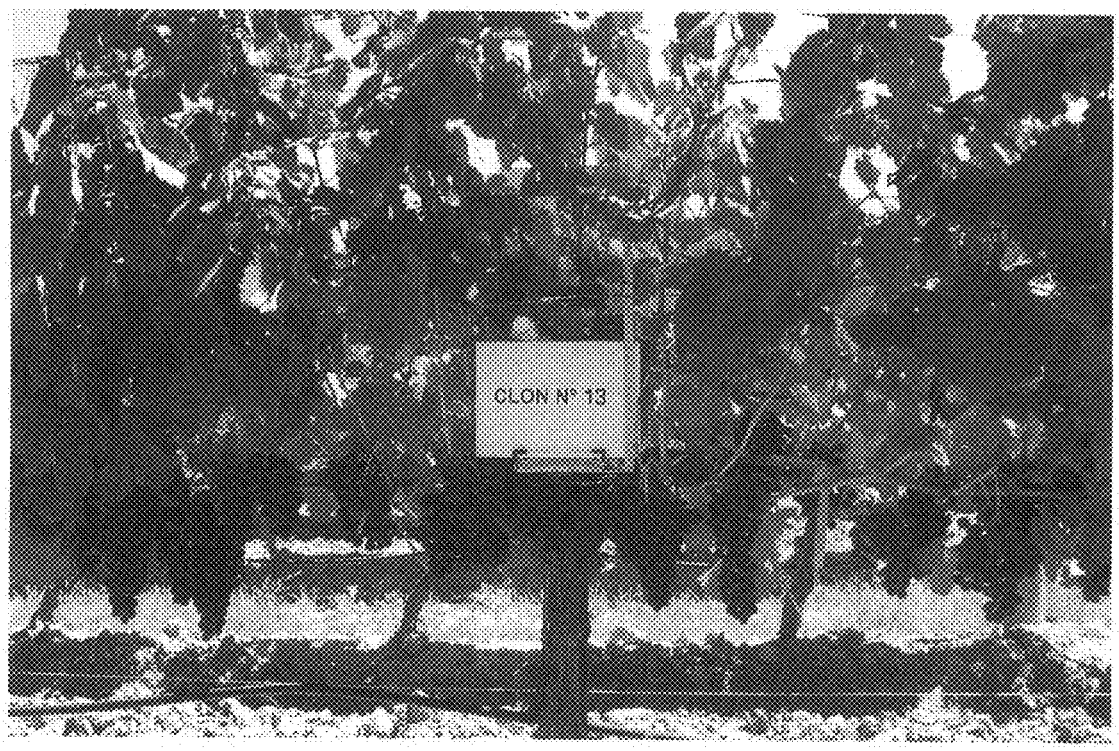
FIG. 5: Photograph showing the grape variety 'Catena Malbec Clone 13'.

FIG. 5 is a photograph of the vine with fruit from grape variety 'Catena Malbec Clone 13'.

What is claimed is:

1. A novel and distinct variety of Malbec grapevine herein denominated 'Catena Malbec Clone 13' having the characteristics described and illustrated herein.

* * * * *